(12) United States Patent
Hwang et al.

(10) Patent No.: US 10,577,462 B2
(45) Date of Patent: Mar. 3, 2020

(54) PRODUCTION METHOD OF POLY(ALKYLENE CARBONATE) PARTICLES

(71) Applicant: LG CHEM, LTD., Seoul (KR)

(72) Inventors: Woo Sung Hwang, Daejeon (KR); Jong-Ku Lee, Daejeon (KR); Seung Young Park, Daejeon (KR); Dong Kwon Lee, Daejeon (KR); Hyun Ju Cho, Daejeon (KR); Kwang Hyon Kim, Daejeon (KR); Yong Hee An, Daejeon (KR); Jun Wye Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 104 days.

(21) Appl. No.: 15/503,934

(22) PCT Filed: Nov. 4, 2015

(86) PCT No.: PCT/KR2015/011790
§ 371 (c)(1),
(2) Date: Feb. 14, 2017

(87) PCT Pub. No.: WO2016/072741
PCT Pub. Date: May 12, 2016

(65) Prior Publication Data
US 2017/0275423 A1     Sep. 28, 2017

(30) Foreign Application Priority Data

Nov. 4, 2014 (KR) .......................... 10-2014-0152104
Nov. 3, 2015 (KR) .......................... 10-2015-0153887

(51) Int. Cl.
*C08G 64/34* (2006.01)
*C08G 64/40* (2006.01)
*C08J 3/07* (2006.01)
*C07F 3/06* (2006.01)
*C08G 64/16* (2006.01)

(52) U.S. Cl.
CPC ............ *C08G 64/34* (2013.01); *C08G 64/403* (2013.01); *C08J 3/07* (2013.01); *C07F 3/06* (2013.01); *C08G 64/16* (2013.01)

(58) Field of Classification Search
CPC ...... C08G 64/34; C08G 64/403; C08G 64/16; C08J 3/07; C07F 3/06
See application file for complete search history.

(56) References Cited

U.S. PATENT DOCUMENTS

| | | | |
|---|---|---|---|
| 4,668,768 A | 5/1987 | Mendiratta et al. | |
| 4,981,948 A | 1/1991 | Kawachi et al. | |
| 5,041,469 A | 8/1991 | Hostetler et al. | |
| 5,182,363 A | 1/1993 | Asoh et al. | |
| 5,196,507 A | 3/1993 | Totani et al. | |
| 2009/0240025 A1 | 9/2009 | Fujimoto et al. | |

FOREIGN PATENT DOCUMENTS

| | | |
|---|---|---|
| CN | 101437869 A | 5/2009 |
| CN | 103102481 A | 5/2013 |
| JP | 3118833 B2 | 12/2000 |
| JP | 2006-002063 A | 1/2006 |
| JP | 2006002063 A | 1/2006 |
| JP | 2006-257374 A | 9/2006 |
| JP | 2007-126547 A | 5/2007 |
| KR | 10-1990-0002836 A | 3/1990 |
| KR | 1996-0000571 B1 | 1/1996 |
| KR | 10-0810123 B1 | 3/2008 |
| KR | 10-2009-0025219 A | 3/2009 |
| KR | 10-2013-0044223 A | 5/2013 |
| WO | 2014-108517 A2 | 7/2014 |

*Primary Examiner* — Shane Fang
(74) *Attorney, Agent, or Firm* — Dentons US LLP

(57) ABSTRACT

The present invention relates to a production method of polyalkylene carbonate particles capable of precipitating and separating resin particles from a polyalkylene carbonate suspension obtained through polymerization of an epoxide and carbon dioxide. According to the present invention, the production method is capable of obtaining a polyalkylene carbonate resin having excellent workability with a high yield and a low energy cost while reducing a scale of a facility, a processing time, and a wastewater amount, as compared to conventional methods such as a flash separation method.

5 Claims, No Drawings

PRODUCTION METHOD OF POLY(ALKYLENE CARBONATE) PARTICLES

CROSS-REFERENCE TO RELATED APPLICATION

This application is a National Stage Entry of International Application No. PCT/KR2015/008497, filed Aug. 13, 2015, and claims the benefit of and priority to Korean Patent Application No. KR 10-2014-0152104, filed on Nov. 4, 2014, and Korean Patent Application No. 10-2015-0153887 filed on Nov. 3, 2015, all of which are hereby incorporated by reference in their entirety for all purposes as if fully set forth herein.

TECHNICAL FIELD

The present invention relates to a production method of polyalkylene carbonate particles.

BACKGROUND OF ART

Since the industrial revolution, modern society has been built by consuming a large amount of fossil fuels, however, the atmospheric concentration of carbon dioxide has correspondingly increased, and this increase is more accelerated by environmental destruction such as deforestation, etc.

Global warming is caused by an increase of greenhouse gases such as carbon dioxide, Freon, and methane in the atmosphere. Thus, it is very important to reduce the atmospheric concentration of carbon dioxide which significantly contributes to global warming, and various researches into emission regulation, immobilization, etc., have been conducted on a global scale.

Among them, a copolymerization reaction of carbon dioxide and epoxide discovered by Inoue et al., has been expected as a reaction to solve the global warming problem, and has been actively researched not only in view of fixation of chemical carbon dioxide but also in view of the use of carbon dioxide as a carbon source.

In particular, in recent years, the polyalkylene carbonate resin obtained by the polymerization of carbon dioxide and epoxide has received much attention as a kind of biodegradable resin.

In the production of the polyalkylene carbonate resin, solution polymerization in which reaction heat and molecular weight are easily controlled is generally used.

However, in the solution polymerization process, viscosity increases rapidly as a solid content included in a solution increases, and thus there is a great restriction in performing subsequent processes.

Further, an amount of loss during filtration and transfer processes of the solution is increased due to the high viscosity of the solution, which reduces a yield of a final resin.

On the other hand, a process of removing the solvent is required in the production of the resin by solution polymerization.

However, in a conventional method (flash separation method) in which a solvent is volatilized by increasing a temperature of a solution, a solution in which a polymer is dispersed in the solvent has remarkably reduced volatilization efficiency of the solvent as compared to that of a pure solvent.

Accordingly, when the resin is produced by the solution polymerization, the process of removing the solvent using the flash separation method has problems in that a processing time is long, and a lot of energy is consumed.

In particular, since the polyalkylene carbonate resin is able to be easily decomposed by heat, there are various restrictions on the process of separating the solvent by heat.

For example, when the temperature of the flash separation process is lowered to prevent the decomposition of the resin, removal efficiency of the solvent is rapidly decreased. When a facility is configured in multi-stages to increase efficiency, a large capacity facility is required.

Further, in order to recover the solvent and monomers gasified in the flash separation process, there are drawbacks in that operation of a freezing condenser, etc., is required, which increases operation cost.

In addition, a pelletizing process by extrusion is required to ensure workability of a resin in the production of the polyalkylene carbonate resin.

However, when the alkylene carbonate produced in the polymerization is included in the resin at a certain level or more, the pelletizing process cannot be performed.

Therefore, it is essential to perform a washing process for removing the alkylene carbonate included in the resin prior to performing the pelletizing process.

However, there is a problem in that a large amount of wastewater occurs in the washing process, and thus the cost of treating wastewater is increased.

DETAILED DESCRIPTION OF THE INVENTION

[Technical Problem]

The present invention has been made in an effort to provide a production method of polyalkylene carbonate particles having advantages of effectively precipitating and separating resin particles from a polyalkylene carbonate suspension obtained through polymerization of an epoxide and carbon dioxide.

[Technical Solution]

An exemplary embodiment of the present invention provides a production method of polyalkylene carbonate particles, including:

forming a polyalkylene carbonate suspension by polymerizing a monomer including an epoxide and carbon dioxide in an organic solvent in which an organic zinc catalyst is present; and precipitating the polyalkylene carbonate particles by mixing the suspension with a solution including an organic antisolvent with respect to polyalkylene carbonate and water at a weight ratio of 1:3 to 1:10, under agitation at 250 to 500 rpm, wherein the suspension is mixed so that a solid included in the suspension has a weight ratio of 1:0.5 to 1:2 with respect to the organic antisolvent.

Hereinafter, a production method of polyalkylene carbonate particles according to an exemplary embodiment of the present invention is described in detail.

Unless specifically indicated, technical terms used in the present specification are intended to describe specific exemplary embodiments, and should not be interpreted as limiting the present invention.

In addition, singular forms used herein include plural forms unless the phrases have clearly opposite meanings.

The term "including" used herein specifies specific characteristics, regions, integers, steps, operations, elements, and/or components, but it does not exclude the presence or the addition of other specific characteristics, regions, integers, steps, operations, elements, components, and/or groups. In addition, the term "antisolvent" as used throughout the present specification means a solvent which precipitates an optional product as a solid phase due to rapidly reduced solubility in a state in which the optional product (for example, a polyalkylene carbonate resin) is dissolved in a solvent.

For example, when the antisolvent is added to a solution in which the optional product is dispersed, the solubility of the product is rapidly reduced, and the product is precipitated.

Then, the precipitated product can be easily separated from the solution by filtration, decanting, centrifugation, or the like.

As a result of continuous experiments by the present inventors, it was surprisingly found that when an organic antisolvent and water are added to a polyalkylene carbonate suspension obtained by polymerizing a monomer including an epoxide and carbon dioxide in an organic solvent, a solid included in the suspension is precipitated (crystallized).

In addition, it was confirmed that granular polyalkylene carbonate particles having excellent workability could be obtained when an appropriate agitation force is applied during the precipitation process of the solid.

Regarding this, in order to separate the solid from the polyalkylene carbonate suspension obtained through the solution polymerization, a step of removing the organic solvent used in the solution polymerization is essential.

However, the polyalkylene carbonate resin is characterized by being easily decomposed by heat.

Accordingly, in a conventional method in which an organic solvent is volatilized by increasing a temperature of the suspension as in a flash separation method, a heating temperature cannot be increased to have a specific range or more, and thus a large capacity facility for treating the solvent in a mild temperature condition is required, a processing time is increased, and a lot of energy is consumed.

Further, in the flash separation method, a large amount of wastewater inevitably occurs in the washing process for removing the alkylene carbonate included in the polyalkylene carbonate resin, and thus there is a drawback in that a great deal of cost is required for wastewater treatment.

In addition, in the flash separation method, since the polyalkylene carbonate resin is obtained in a form having a remarkably low workability, it is not easy to handle the resin in subsequent processes, and thus a pelletizing process, etc., are essentially required.

The production method of the polyalkylene carbonate particles provided by the present invention is a method for precipitating (crystallizing) and separating the granular resin particles from the polyalkylene carbonate suspension by using the organic antisolvent.

That is, the method according to the present invention is a method for obtaining granular resin particles by controlling the solubility of the polymer with respect to the organic solvent, precipitating the particles, and simultaneously applying an appropriate agitation force.

This production method may more easily separate the solid from the suspension and may also obtain granular resin particles having excellent workability, as compared to the conventional flash separation method.

In particular, the precipitation of the resin particles and volatilization of the organic solvent may be simultaneously achieved in the production method according to the present invention, and thus a process time may be shortened, energy consumption may be reduced, and a large scale facility such as a rotating disc contactor (RDC) column may not be required, thereby reducing a scale of the facility.

In addition, since the production method according to the present invention may relatively easily remove the alkylene carbonate included in the polyalkylene carbonate particles, a wastewater amount in the washing process is small.

Further, the granular resin particles obtained through the above-described production method according to the present invention may minimize the loss during a transfer process in the production process, and thus a relatively high yield may be secured.

According to an embodiment of the present invention, a production method of polyalkylene carbonate particles includes:

forming a polyalkylene carbonate suspension by polymerizing a monomer including an epoxide and carbon dioxide in an organic solvent in which an organic zinc catalyst is present; and precipitating the polyalkylene carbonate particles by mixing the suspension with a solution including an organic antisolvent with respect to polyalkylene carbonate and water at a weight ratio of 1:3 to 1:10, under agitation at 250 to 500 rpm, wherein the suspension is mixed so that a solid included in the suspension has a weight ratio of 1:0.5 to 1:2 with respect to the organic antisolvent.

Hereinafter, respective steps that may be included in the production method of the polyalkylene carbonate particles according to an exemplary embodiment of the present invention are described.

In the production method, the forming of the polyalkylene carbonate suspension may be performed by a method of polymerizing a monomer including an epoxide and carbon dioxide in an organic solvent in which an organic zinc catalyst is present.

That is, the polyalkylene carbonate suspension may be obtained by solution polymerization of the monomer including an epoxide and carbon dioxide, wherein the organic zinc catalyst may be used.

The organic zinc catalyst may be fine crystalline particles that may be obtained by reacting a zinc precursor with a C3-C20 dicarboxylic acid, and may be general organic zinc catalysts in the art to which the present invention pertains, such as zinc glutarate.

Here, zinc oxide, zinc sulfate ($ZnSO_4$), zinc chlorate ($Zn(ClO_3)_2$), zinc nitrate ($Zn(NO_3)_2$), zinc acetate ($Zn(OAc)_2$), zinc hydroxide, or the like, may be used as the zinc precursor.

In addition, as the dicarboxylic acid, an aliphatic dicarboxylic acid selected from the group consisting of malonic acid, glutaric acid, succinic acid, and adipic acid may be used, or an aromatic dicarboxylic acid selected from the group consisting of terephthalic acid, isophthalic acid, homophthalic acid, and phenylglutaric acid may be used.

However, in view of activity of the catalyst, etc., the glutaric acid may be suitably used as the dicarboxylic acid, and the zinc dicarboxylate-based organic zinc catalyst may preferably be a zinc glutarate-based catalyst.

The organic zinc catalyst may be added at a molar ratio of about 1:50 to 1:1000 relative to the epoxide.

More preferably, the organic zinc catalyst may be added at a molar ratio of about 1:70 to 1:600, or about 1:80 to 1:300, relative to the epoxide.

That is, when the molar ratio of the organic zinc catalyst to the epoxide is excessively low, it may be difficult to exhibit sufficient catalytic activity in the solution polymerization.

However, when the molar ratio of the organic zinc catalyst to the epoxide is excessively high, it is not efficient since the catalyst is excessively used, by-products may occur, or back-biting of the resin may occur due to heating in the presence of the catalyst.

Further, in the solution polymerization, any solvent capable of copolymerizing the monomer including the epoxide and carbon dioxide may be used as the organic solvent.

For example, the organic solvent may be at least one compound selected from the group consisting of dichloromethane, dichloroethane, chloroform, acetonitrile, methyl acetate, ethylacetate, propyl acetate, isopropyl acetate, vinyl acetate, methylethylketone, methylpyrrolidone, dimethyl sulfoxide, nitromethane, nitropropane, caprolactone, acetone, polypropylene oxide, tetrahydrofuran, benzene, and styrene.

Here, the organic solvent may be used at a weight ratio of about 1:0.5 to 1:100, and preferably, at a weight ratio of about 1:1 to 1:10, relative to the epoxide.

That is, when the weight ratio of the organic solvent to the epoxide is excessively low as less than about 1:0.5, the organic solvent does not function properly as a reaction medium, and thus it may be difficult to have advantages of the solution polymerization (for example, effects of controlling reaction heat and a molecular weight of a resin).

However, when the weight ratio of the organic solvent to the epoxide is more than about 1:100, a concentration of the epoxide may be relatively low, resulting in a decrease in productivity, and a molecular weight of a finally formed resin may be reduced or a side reaction may be increased.

As the epoxide in the monomer, at least one compound selected form the group consisting of a C2-C20 alkylene oxide unsubstituted or substituted with a halogen or a C1-C5 alkyl group; a C4-C20 cycloalkylene oxide unsubstituted or substituted with a halogen or a C1-C5 alkyl group; and a C8-C20 styrene oxide unsubstituted or substituted with a halogen or a C1-C5 alkyl group may be used.

Representatively, as the epoxide, a C2-C20 alkylene oxide unsubstituted or substituted with a halogen or a C1-C5 alkyl group may be used.

Specific examples of the epoxide according to the present invention include ethylene oxide, propylene oxide, butene oxide, pentene oxide, hexene oxide, octene oxide, decene oxide, dodecene oxide, tetradecene oxide, hexadecene oxide, octadecene oxide, butadiene monoxide, 1,2-epoxy-7-octene, epifluorohydrine, epichlorohydrine, epibromohydrine, isopropyl glycidyl ether, butyl glycidyl ether, t-butyl glycidyl ether, 2-ethylhexyl glycidyl ether, allyl glycidyl ether, cyclopentene oxide, cyclohexene oxide, cyclooctene oxide, cyclododecene oxide, alpha-pinene oxide, 2,3-epoxy norbornene, limonene oxide, dieldrin, 2,3-epoxypropylbenzene, styrene oxide, phenylpropylene oxide, stilbene oxide, chlorostilbene oxide, dichlorostilbene oxide, 1,2-epoxy-3-phenoxypropane, benzyloxymethyl oxirane, glycidyl-methylphenyl ether, chlorophenyl-2,3-epoxypropyl ether, epoxypropyl methoxyphenyl ether, biphenyl glycidyl ether, glycidyl naphthyl ether, and the like.

Most representatively, ethylene oxide may be used as the epoxide.

Further, an amount of the carbon dioxide in the monomer is not particularly limited.

However, in consideration of the efficiency of the polymerization reaction, the carbon dioxide may be added at 0.1 to 20 MPa, 0.1 to 10 MPa, or 0.1 to 5 MPa.

Further, the solution polymerization may be performed at about 50 to 100° C. and about 15 to 50 bar for about 1 to 60 h.

In addition, the solution polymerization may more preferably be performed at about 70 to 90° C. and about 20 to 40 bar for about 3 to 40 hours.

Since remaining polymerization processes and conditions except for the above description may follow general polymerization conditions, etc., for producing the polyalkylene carbonate resin, and additional descriptions thereof will be omitted.

Further, a step of precipitating the polyalkylene carbonate particles from the polyalkylene carbonate suspension obtained through the above-described solution polymerization is performed.

In general, a method for evaporating the organic solvent by heating the suspension (flash separation method) is performed as a method for obtaining the polyalkylene carbonate resin from the suspension.

However, in the production method according to an exemplary embodiment of the present invention, an organic antisolvent and water are added to the suspension to precipitate (crystallize) the solid included in the suspension, and an appropriate agitation force is applied in the process, thereby obtaining the polyalkylene carbonate particles.

Through these processes, granular polyalkylene carbonate particles having excellent workability may be obtained.

The organic antisolvent is any organic solvent in which the polyalkylene carbonate resin is not dissolved, and may have a higher boiling point and an opposite polarity as compared to those of the organic solvent used in the solution polymerization.

As a non-limiting example, the organic antisolvent may be at least one compound selected from the group consisting of n-heptane, n-hexane, cyclohexane, and diethyl ether; alcohols such as methanol, ethanol, propyl alcohol, and butyl alcohol; and glycols such as ethylene glycol, propylene glycol, etc.

When dichloroethane is used as the solvent in the synthesis of the polyalkylene carbonate resin as a non-limiting example, the organic antisolvent may suitably be n-heptane and n-hexane.

When the organic antisolvent and water are added to the polyalkylene carbonate suspension and agitated, solubility of the solid (polyalkylene carbonate resin) dispersed in the suspension is rapidly decreased and precipitated as a solid phase.

In addition, this process may be performed at a temperature that is higher than a boiling point of the organic solvent and lower than a boiling point of the organic antisolvent, and thus the precipitation of the solid and the volatilization of the organic solvent may be simultaneously performed.

In particular, the process may be performed under a suitable agitation force to control a nucleation rate, and thus the solid may be precipitated in granular forms.

According to an exemplary embodiment of the present invention, in order to obtain the above-described effects, requirements such as a content ratio of the organic antisolvent and water mixed with the suspension, a content ratio of the solid and the organic antisolvent included in the suspension, and an agitation force provided in the process are required to be simultaneously satisfied.

Among the requirements, a weight ratio of the organic antisolvent and water included in the solution mixed with the suspension is 1:3 to 1:10, and preferably 1:3 to 1:5.

That is, when the content of water mixed with the suspension is excessively small, a ratio of a water layer due to phase separation is low, which may be disadvantageous for recovering the precipitated resin particles.

However, when the content of water mixed with the suspension is excessively large, energy consumption required for heating is increased, which may be disadvantageous in view of efficiency and cost.

In addition, it is preferable that the suspension is mixed so that the solid included in the suspension has a weight ratio of 1:0.5 to 1:2, preferably 1:0.5 to 1:1.5, and more preferably 1:1, with respect to the organic antisolvent.

That is, when an amount of the organic antisolvent to be mixed is excessively small relative to the solid included in the suspension, it may be disadvantageous since the precipitation of the solid is not sufficiently performed.

However, when the organic antisolvent is mixed excessively, precipitation of the solid may be excessively and rapidly performed, and thus it may be impossible to obtain the resin particles in granular forms.

Here, the content of the solid in the suspension may be measured using general facilities such as a halogen moisture analyzer.

In particular, the step of precipitating the solid is preferably performed under agitation at 250 to 500 rpm, preferably 250 to 450 rpm, and more preferably 350 to 400 rpm.

That is, when the agitation force on the mixture of the suspension, the organic antisolvent and water is excessively weak, the solid to be precipitated is aggregated into a lump and precipitated, and thus resin particles having uniform size may not be obtained.

In contrast, when the agitation force is excessively strong, the resin particles may have excessively small sizes, which may cause problems in subsequent solid-liquid separation.

The step of precipitating the solid may be performed at a temperature that is higher than the boiling point of the organic solvent and lower than the boiling point of the organic antisolvent, and thus the precipitation of the solid and the volatilization of the organic solvent may be simultaneously performed.

The temperature may be determined in consideration of the boiling point of the organic solvent and the organic antisolvent used in the solution polymerization, and thus the temperature is not particularly limited.

However, according to an exemplary embodiment of the present invention, in consideration of characteristics of the polyalkylene carbonate which is vulnerable to heat and a volatilization efficiency of the organic solvent, it is preferable that the temperature is 45 to 70° C., preferably 50 to 65° C., and more preferably, 60 to 65° C.

In addition, kinds of the organic solvent and the organic antisolvent may be determined in consideration of the temperature.

After the step of precipitating the solid, a dehydration process of removing a liquid material, a washing step of removing by-products (for example, alkylene carbonate, etc.) included in the precipitated resin particles, etc., may be performed. By performing these processes, the polyalkylene carbonate particles in granular forms may be obtained.

Since the polyalkylene carbonate particles are obtained in the granular forms, it is easy to handle in the dehydration and washing processes described above, and there is no loss of the amount, and thus it is possible to secure a high yield.

Further, the granular polyalkylene carbonate itself has excellent workability, and in some cases, may be used as a raw material for various products without performing a separate processing step such as palletizing.

[Advantageous Effects]

According to the present invention, a production method capable of obtaining a polyalkylene carbonate resin having excellent workability with a high yield and a low energy cost while reducing a scale of facility, a processing time, and a waste water amount as compared to conventional methods such as a flash separation method is provided.

DETAILED DESCRIPTION OF THE EMBODIMENTS

Hereinafter, preferable examples of the present invention will be provided for better understanding of the present invention. However, the following examples are provided only for illustration of the present invention, and should not be construed as limiting the present invention by the examples.

Preparation Example

As described below, a polyethylene carbonate suspension was obtained by copolymerizing ethylene oxide and carbon dioxide using a zinc-glutarate catalyst.

Here, all operations using compounds sensitive to air or water were performed using a standard Schlenk technique or a dry box technique.

First, purified dichloromethane (1.78 kg) as a solvent was added to a high-pressure reactor equipped with an agitator.

A dry zinc-glutarate catalyst (18.5 g) and purified ethylene oxide (330 g) were added to the reactor, and the reactor was filled to a pressure of about 10 atm with carbon dioxide and agitated for 10 min.

Then, carbon dioxide was added again until a total amount of carbon dioxide reached 410 g, a temperature was raised to 70° C., and the mixture was reacted for 5 h while agitating at 50 rpm.

Considering that the carbon dioxide was continuously consumed as the copolymerization proceeded, carbon dioxide was continuously added to the reactor at a flow rate of 105 g/h.

After the reaction, unreacted carbon dioxide and ethylene oxide were blown off in a gas phase to be removed.

In addition, in order to facilitate the filtering of a catalyst residue in the solution by reducing a concentration of residual ethylene oxide and simultaneously reducing the viscosity, 3.22 kg of dichloromethane was further added to the reactor, thereby obtaining a polyethylene carbonate suspension having a solid content of about 10 to 15%.

Example 1

The polyethylene carbonate suspension obtained through the above preparation example was passed through polymer filters to remove the catalyst included in the suspension, and then transferred to a reaction chamber for precipitation (crystallization) of polyethylene carbonate at a flow rate of about 20 kg/h.

Here, 2 kg of water and 0.5 kg of n-heptane as an organic antisolvent with respect to polyethylene carbonate were previously added to the reaction chamber, and strongly agitated at 400 rpm while maintaining the temperature at 60° C.

That is, the suspension was added to the reaction chamber so that the organic antisolvent, the water, and the polyethylene carbonate (based on the solid content of the suspension) were mixed at a weight ratio of 1:4:1.

Through this process, precipitation of the solid proceeded.

Since volatilization of the organic solvent included in the suspension proceeded from the start of the addition of the suspension to the chamber, a vent line at the top of the chamber connected to a condenser was opened at this time.

This process was continued until no more flow was observed on the vent line.

Subsequently, the liquid material remaining in the precipitate was removed using a dehydrator to obtain polyethylene carbonate granules.

The polyethylene carbonate granules were transferred to a washing chamber.

At this time, 500 g of fresh water was pre-filled in the washing chamber, agitated at 100 rpm, and washed for about 30 min.

Then, water was removed again through the dehydrator, and then the washed granules were put into an extruder of which a temperature was set.

When it was confirmed that the granules passed through the extruder and were discharged, the cutter was connected to obtain a polyethylene carbonate resin in a pellet form.

Example 2

Polyethylene carbonate granules and a resin in a pellet form, including the granules, were obtained in the same manner as in Example 1, except that the washing process of the polyethylene carbonate granules was performed twice in the washing chamber.

Example 3

Example 3 was performed in the same manner as in Example 1, except that an agitation speed in the reaction chamber was adjusted to 250 rpm in the process of precipitating the solid of the suspension.

Example 4

Example 4 was performed in the same manner as in Example 1, except that an agitation speed in the reaction chamber was adjusted to 500 rpm in the process of precipitating the solid of the suspension.

Example 5

Example 5 was performed in the same manner as in Example 1, except that a weight ratio of n-heptane, water, and polyethylene carbonate (based on the solid content of the suspension) in the reaction chamber was adjusted to be 1:3:0.5.

Example 6

Example 6 was performed in the same manner as in Example 1, except that a weight ratio of n-heptane, water, and polyethylene carbonate (based on the solid content of the suspension) in the reaction chamber was adjusted to be 1:10:2.

Example 7

Example 7 was performed in the same manner as in Example 1, except that a weight ratio of n-heptane, water, and polyethylene carbonate (based on the solid content of the suspension) in the reaction chamber was adjusted to be 1:4:2.

Comparative Example 1

Comparative Example 1 was performed in the same manner as in Example 1, except that n-heptane as an antisolvent was not added.

However, since the polyethylene carbonate granules were not formed by the method of Comparative Example 1, the washing process and the subsequent processes of Example 1 could not be performed.

Comparative Example 2

Comparative Example 2 was performed in the same manner as in Example 1, except that 2.5 kg of n-heptane was added to the reaction chamber (i.e., a weight ratio of the antisolvent, water, and polyethylene carbonate (based on the solid content of the suspension) was 1:0.8:0.2).

However, since the polyethylene carbonate granules were not formed by the method of Comparative Example 2, the washing process and the subsequent processes of Example 1 could not be performed.

Comparative Example 3

Comparative Example 3 was performed in the same manner as in Example 1, except that an agitation speed in the reaction chamber was adjusted to 100 rpm in the process of precipitating the solid of the suspension.

However, since the polyethylene carbonate granules were not formed by the method of Comparative Example 3, the washing process and the subsequent processes of Example 1 could not be performed.

Comparative Example 4

Comparative Example 4 was performed in the same manner as in Example 1, except that an agitation speed in the reaction chamber was adjusted to 600 rpm in the process of precipitating the solid of the suspension.

Comparative Example 5

Comparative Example 5 was performed in the same manner as in Example 1, except that a weight ratio of n-heptane, water, and polyethylene carbonate (based on the solid content of the suspension) in the reaction chamber was adjusted to be 1:0.8:1.

Comparative Example 6

Comparative Example 6 was performed in the same manner as in Example 1, except that a weight ratio of n-heptane, water, and polyethylene carbonate (based on the solid content of the suspension) in the reaction chamber was adjusted to be 1:15:1.

Comparative Example 7

Comparative Example 7 was performed in the same manner as in Example 1, except that a weight ratio of n-heptane, water, and polyethylene carbonate (based on the solid content of the suspension) in the reaction chamber was adjusted to be 1:4:0.2.

Comparative Example 8

Comparative Example 8 was performed in the same manner as in Example 1, except that a weight ratio of n-heptane, water, and polyethylene carbonate (based on the solid content of the suspension) in the reaction chamber was adjusted to be 1:4:2.5.

Control Example (Flash Separation Method)

The polyethylene carbonate suspension obtained through the above preparation example was passed through polymer filters to remove the catalyst included in the suspension. Then, for extraction of ethylene carbonate in the suspension, a total of 7.5 kg of fresh water was poured into a rotating disc contactor (RDC) column equipped with 46 multi-stages.

Here, a temperature of the column was set to 20° C. or less in advance.

When the suspension and water were mixed, phase separation occurred, and at this time, only a polymer solution in a lower layer was taken to a next step and processed.

That is, the solution was transferred to a primary flash drum at a flow rate of about 20 kg/h to volatilize the solvent.

Here, the flash drum was heated to 90° C. in advance, and when the polymer was solution started to be added, the vent line at the top connected to the condenser was opened to allow the volatile solvent to condense through the condenser.

Initially, the volatilization proceeded smoothly at a flow rate of 1.0 kg/h or more of the solvent, which was transferred to the condenser. However, since the flow rate was gradually decreased as time passed, vacuum of about 50 to 80 torr was applied from the time when about 3 kg of the solvent remained.

Then, generally, the volatilization flow rate of the solvent almost reached zero from the time when about 1.25 to 1.5 kg of the solvent remained. Accordingly, the vent line of the top was closed to terminate the volatilization.

Then, the polymer solution having a significantly high viscosity due to the volatilization of the solvent was transferred to a secondary flash drum which was heated to 110° C. in advance through a preheater set at 150° C. by operating a gear pump.

Similarly, the vent line of the top was opened to volatilize and condense the solvent, and vacuum of about 30 to 55 torr was applied immediately after the transfer of the polymer solution to the secondary flash drum was completed.

After about 30 min, the vent line of the top was closed to terminate the solvent volatilization, and the gear pump was operated to transfer the polymer solution to a lower extruder.

When it was confirmed that the polymer passed through the extruder and was discharged, the cutter was connected to obtain a pellet-shaped polyethylene carbonate resin.

Experimental Example

1) Measurement of residual ethylene carbonate content: A content of ethylene carbonate remaining in the polyethylene carbonate resin was measured using a nuclear magnetic resonance spectrum (Bruker 600 spectrometer, 1H NMR, 600 MHz).

2) Measurement of solid content: A content of the solid included in the polyethylene carbonate suspension was measured using a halogen moisture analyzer (HB43-S, Mettler Toledo). At this time, water and other solvents were evaporated under a temperature condition of about 110° C., and the remaining solid was weighed.

3) Whether the polyethylene carbonate granules were formed, yields of the polyethylene carbonate resin, volatilization time of the solvent, residual ethylene carbonate contents, and wastewater amounts in the washing process in the examples, comparative examples, and control example are shown in Tables 1 to 3 below.

TABLE 1

|  | Example 1 | Example 2 | Comparative Example 1 | Comparative Example 2 | Comparative Example 3 | Control Example |
|---|---|---|---|---|---|---|
| Granule formation | ○ | ○ | X | X | X | — |
| Yield (%) | 95.63 | 95.12 | — | — | — | 81.34 |
| Solvent volatilization time (min) | 29 | 29 | 113 | 25 | 45 | 137 |
| Residual EC content (wt %) | 0.81 | 0.59 | — | — | — | 0.55 |
| Wastewater amount (kg) | 2.5 | 3.0 | — | — | — | 7.5 |

TABLE 2

|  | Example 3 | Example 4 | Example 5 | Example 6 | Example 7 |
|---|---|---|---|---|---|
| Granule formation | ○ | ○ | ○ | ○ | ○ |
| Yield (%) | 95.58 | 95.66 | 95.69 | 95.20 | 95.16 |
| Solvent volatilization time (min) | 37 | 27 | 28 | 31 | 35 |
| Residual EC content (wt %) | 1.01 | 0.80 | 0.78 | 0.85 | 1.35 |
| Wastewater amount (kg) | 2.5 | 2.5 | 3.5 | 3.0 | 1.5 |

TABLE 3

|  | Comparative Example 4 | Comparative Example 5 | Comparative Example 6 | Comparative Example 7 | Comparative Example 8 |
|---|---|---|---|---|---|
| Granule formation | X | X | ○ | X | X |
| Yield (%) | — | — | 95.64 | — | — |
| Solvent volatilization time (min) | 26 | 67 | 29 | 25 | 54 |
| Residual EC content (wt %) | — | — | 0.72 | — | — |
| Wastewater amount (kg) | — | — | 8.0 | — | — |

In Examples 1 to 7, the polyethylene carbonate particles were well formed in granular forms, and smoothly proceeded to the washing process, the dehydration process, and the extrusion process.

In particular, it was confirmed that the most preferable results were obtained in Examples 1 and 2.

In Example 3, the volatilization time of the solvent was longer and the residual EC content was slightly higher due to the relatively slow agitation speed as compared to Example 1.

In Example 4, the agitation speed was relatively fast, and thus, although not shown in the table above, the particles were formed in a slightly smaller particle size, and uniformity of the size was deteriorated, such that transfer efficiency to the next process was slightly reduced.

In Examples 5 and 6, since the amount of water was relatively large, the wastewater amount increased, and the efficiency was slightly lower than that in Example 1.

Further, in Examples 6 and 7, the solid content was slightly high, and thus the yield, the volatilization time of the solvent, and the residual EC content were not as good as those of Example 1.

In addition, the examples had a high yield of about 95% or more.

As compared to these examples, when the antisolvent was not added as in Comparative Example 1, the solid was not well precipitated, and when the excessive antisolvent was added as in Comparative Example 2, or when the agitation speed was slow in the induction of precipitation as in Comparative Example 3, the solid was aggregated into a lump, and precipitated.

When the agitation speed was excessively high as in Comparative Example 4, the particles were formed with an excessively small size, and as a result, a surface area of the particles was relatively and excessively increased, and the granules were not maintained in the dehydration process, but were re-aggregated into a lump.

When the water content was excessively low as in Comparative Example 5, even if the polymer was precipitated as granules, the granules could not be dispersed in water, and were aggregated into a lump.

In Comparative Example 6, the granules were formed, but the wastewater amount was excessively large.

In Comparative Example 7, the amount of the antisolvent was excessively high, and thus the precipitation proceeded rapidly, resulting in aggregation of the particles into a lump.

In Comparative Example 8, the polymer was not precipitated in the granular form due to an insufficient amount of the antisolvent, was precipitated like a thread, and was aggregated again in the dehydration process.

In addition, it was confirmed that, as compared to the conventional flash separation method according to the control example, the time required for the solvent volatilization in the examples was reduced to ¼ or less, thereby reducing energy cost.

Further, the examples had a wastewater amount as low as half or less while showing a similar level of residual ethylene carbonate content, as compared to the control example.

The invention claimed is:

1. A production method of polyalkylene carbonate particles, comprising:
    forming a polyalkylene carbonate suspension by polymerizing a monomer including an epoxide and carbon dioxide in an organic solvent in which an organic zinc catalyst is present; and
    precipitating the polyalkylene carbonate particles by mixing the polyalkylene carbonate suspension with a solution including an organic antisolvent with respect to polyalkylene carbonate and water at a weight ratio of 1:3 to 1:10, under agitation at 250 to 500 rpm,
    wherein the polyalkylene carbonate suspension is mixed with the solution so that a solid included in the polyalkylene carbonate suspension has a weight ratio of 1:0.5 to 1:2 with respect to the organic antisolvent,
    wherein the organic antisolvent is a compound having a higher boiling point than that of the organic solvent, and an opposite polarity to that of the organic solvent,
    wherein the organic solvent is at least one compound selected from the group consisting of acetonitrile, methyl acetate, ethyl acetate, propyl acetate, isopropyl acetate, acetone, and tetrahydrofuran, and
    wherein the organic antisolvent is at least one compound selected from the group consisting of n-heptane, n-hexane, cyclohexane, diethylether, methanol, ethanol, propyl alcohol, butanol, ethylene glycol, and propylene glycol.

2. The production method of claim 1, wherein the precipitating of the polyalkylene carbonate particles is performed at a temperature that is higher than a boiling point of the organic solvent and lower than a boiling point of the organic antisolvent.

3. The production method of claim 1, wherein the organic zinc catalyst is used at a molar ratio of 1:50 to 1:1000 with respect to the epoxide.

4. The production method of claim 1, wherein the organic solvent is used at a weight ratio of 1:0.5 to 1:100 with respect to the epoxide.

5. The production method of claim 1, wherein the forming of the polyalkylene carbonate suspension is performed at 50° C. to 100° C.

* * * * *